(12) United States Patent
Artaki et al.

(10) Patent No.: US 11,793,558 B2
(45) Date of Patent: Oct. 24, 2023

(54) ALL IN ONE PLATE HOLDER AND SPRING LOADED AWL

(71) Applicant: K2M, Inc., Leesburg, VA (US)

(72) Inventors: Alexander Horia Artaki, Bremerton, WA (US); Joseph Michael Meyer, Bethel, OH (US); Pauline Patricia Hutton, Gainesville, VA (US); Joshua David Rubin, Reston, VA (US); Chambliss Harrod, Baton Rouge, LA (US); Stephen Tolhurst, Flower Mound, TX (US)

(73) Assignee: K2M, Inc., Leesburg, VA (US)

( * ) Notice: Subject to any disclaimer, the term of this patent is extended or adjusted under 35 U.S.C. 154(b) by 404 days.

(21) Appl. No.: 17/003,243

(22) Filed: Aug. 26, 2020

(65) Prior Publication Data

US 2021/0059726 A1    Mar. 4, 2021

Related U.S. Application Data

(60) Provisional application No. 62/894,118, filed on Aug. 30, 2019.

(51) Int. Cl.
*A61B 17/80* (2006.01)
*A61B 17/70* (2006.01)
*A61B 17/92* (2006.01)

(52) U.S. Cl.
CPC ........ *A61B 17/808* (2013.01); *A61B 17/7059* (2013.01); *A61B 17/92* (2013.01)

(58) Field of Classification Search
CPC .............. A61B 17/1604; A61B 17/808; A61B 17/8872
See application file for complete search history.

(56) References Cited

U.S. PATENT DOCUMENTS

| 2,338,765 A | 1/1944 | Hartman |
| 3,682,177 A | 8/1972 | Ames et al. |
| 4,878,915 A | 11/1989 | Brantigan |

(Continued)

FOREIGN PATENT DOCUMENTS

| EP | 1985249 A1 | 10/2008 |
| WO | 2007019873 A1 | 2/2007 |

(Continued)

OTHER PUBLICATIONS

European Search Report for Application No. EP 20193495.7, dated Jan. 26, 2021, 8 pages.

*Primary Examiner* — David W Bates
(74) *Attorney, Agent, or Firm* — Lerner David LLP

(57) ABSTRACT

In one embodiment, the present disclosure relates to a system that includes a plate holder and an awl. The plate holder has a first end and a second end with an engagement feature at the second end that is engageable with a bone plate. The awl is releasably engaged to the plate holder and includes a locking mechanism adjustable from a first setting to a second setting and a tip. When the locking mechanism is in the first setting, the awl is fixed relative to the plate holder and the tip is disposed within the plate holder. When the locking mechanism is in the second setting, the awl is axially translatable relative to the plate holder such that the tip of the awl extends out of the second end of the plate holder.

20 Claims, 8 Drawing Sheets

(56) References Cited

U.S. PATENT DOCUMENTS

| | | | | |
|---|---|---|---|---|
| 5,351,404 A * | 10/1994 | Smith | | B25H 7/04 |
| | | | | 81/177.85 |
| 5,423,826 A * | 6/1995 | Coates | | A61B 17/1757 |
| | | | | 606/291 |
| 5,957,946 A * | 9/1999 | Shuler | | A61B 17/16 |
| | | | | 30/366 |
| 6,139,550 A * | 10/2000 | Michelson | | A61B 17/80 |
| | | | | 606/295 |
| 6,193,721 B1 * | 2/2001 | Michelson | | A61B 17/7059 |
| | | | | 606/76 |
| 6,319,257 B1 | 11/2001 | Carignan et al. | | |
| 6,375,655 B1 | 4/2002 | Zdeblick et al. | | |
| 6,668,941 B2 | 12/2003 | Phillips et al. | | |
| 6,739,872 B1 | 5/2004 | Turri | | |
| 6,814,734 B2 | 11/2004 | Chappuis et al. | | |
| 6,902,566 B2 | 6/2005 | Zucherman et al. | | |
| 6,923,814 B1 | 8/2005 | Hildebrand et al. | | |
| 7,131,974 B2 | 11/2006 | Keyer et al. | | |
| 7,169,182 B2 | 1/2007 | Errico et al. | | |
| 7,294,134 B2 | 11/2007 | Weber | | |
| 7,338,494 B2 * | 3/2008 | Ryan | | A61B 17/1604 |
| | | | | 606/79 |
| 7,488,327 B2 | 2/2009 | Rathbun et al. | | |
| 7,527,629 B2 | 5/2009 | Link et al. | | |
| 7,575,580 B2 | 8/2009 | Lim et al. | | |
| 7,608,080 B2 | 10/2009 | Shipp et al. | | |
| 7,618,423 B1 | 11/2009 | Valentine et al. | | |
| 7,625,380 B2 | 12/2009 | Drewry et al. | | |
| 7,771,143 B2 | 8/2010 | Bharadwaj et al. | | |
| 7,811,292 B2 | 10/2010 | Lo et al. | | |
| 7,842,038 B2 * | 11/2010 | Haddock | | A61B 17/3472 |
| | | | | 604/164.01 |
| 7,846,210 B2 | 12/2010 | Perez-Cruet et al. | | |
| 7,883,513 B2 * | 2/2011 | Ralph | | A61B 17/1728 |
| | | | | 606/96 |
| 7,901,458 B2 | 3/2011 | DeRidder et al. | | |
| 7,905,886 B1 | 3/2011 | Curran et al. | | |
| 7,998,215 B2 | 8/2011 | Frey et al. | | |
| 8,043,316 B2 | 10/2011 | Hardin | | |
| 8,043,343 B2 | 10/2011 | Miller et al. | | |
| 8,114,092 B2 | 2/2012 | Altarac et al. | | |
| 8,142,435 B2 | 3/2012 | Refai et al. | | |
| 8,142,441 B2 | 3/2012 | Refai et al. | | |
| 8,206,449 B2 | 6/2012 | Jansen et al. | | |
| 8,216,316 B2 | 7/2012 | Kirschman | | |
| 8,231,633 B2 | 7/2012 | Lim et al. | | |
| 8,298,235 B2 | 10/2012 | Grinberg et al. | | |
| 8,343,195 B2 | 1/2013 | Rathbun et al. | | |
| 8,394,101 B2 | 3/2013 | Landes | | |
| 8,425,530 B2 | 4/2013 | Winslow et al. | | |
| 8,449,463 B2 | 5/2013 | Nunley et al. | | |
| 8,480,682 B2 | 7/2013 | Howlett et al. | | |
| 8,491,598 B2 | 7/2013 | Crook | | |
| 8,491,654 B2 | 7/2013 | Frey et al. | | |
| 8,540,725 B2 | 9/2013 | Lim et al. | | |
| 8,579,910 B2 | 11/2013 | Hester et al. | | |
| 8,602,777 B2 | 12/2013 | Way et al. | | |
| 8,636,804 B2 | 1/2014 | Errico et al. | | |
| 8,696,681 B2 | 4/2014 | Harris et al. | | |
| 8,709,086 B2 | 4/2014 | Glerum | | |
| 8,740,983 B1 | 6/2014 | Arnold et al. | | |
| 8,808,304 B2 | 8/2014 | Weiman et al. | | |
| 8,814,880 B2 | 8/2014 | McAllister et al. | | |
| 8,876,835 B2 | 11/2014 | Petit | | |
| 8,906,097 B2 | 12/2014 | Mather et al. | | |
| 9,138,279 B2 | 9/2015 | Laposta et al. | | |
| 9,254,160 B2 * | 2/2016 | Pakzaban | | A61B 17/8875 |
| 9,301,854 B2 | 4/2016 | Moskowitz et al. | | |
| 9,327,359 B2 | 5/2016 | Wotruba | | |
| 9,339,321 B2 | 5/2016 | Stoll et al. | | |
| 9,351,849 B2 | 5/2016 | Mather et al. | | |
| 9,381,045 B2 | 7/2016 | Donner et al. | | |
| 9,510,957 B2 | 12/2016 | Weiman et al. | | |
| 9,572,589 B2 * | 2/2017 | Knape | | A61B 17/17 |
| 9,603,610 B2 | 3/2017 | Richter et al. | | |
| 9,615,838 B2 * | 4/2017 | Nino | | A61B 17/3496 |
| 9,622,759 B2 | 4/2017 | Jansen | | |
| 9,675,337 B2 | 6/2017 | Gorek et al. | | |
| 9,693,876 B1 | 7/2017 | Mesiwala | | |
| 9,763,675 B2 | 9/2017 | Stoll et al. | | |
| 10,010,314 B2 * | 7/2018 | Karasic | | A61B 17/1633 |
| 10,098,647 B2 | 10/2018 | Nino et al. | | |
| 10,172,626 B2 * | 1/2019 | Paulos | | A61B 17/1604 |
| 10,405,842 B2 | 9/2019 | Kim | | |
| 10,850,193 B2 | 12/2020 | DeRidder et al. | | |
| 2003/0149438 A1 | 8/2003 | Nichols et al. | | |
| 2004/0010259 A1 | 1/2004 | Keller et al. | | |
| 2004/0019353 A1 * | 1/2004 | Freid | | A61B 17/8894 |
| | | | | 606/915 |
| 2004/0098129 A1 | 5/2004 | Lin | | |
| 2005/0015092 A1 * | 1/2005 | Rathbun | | A61B 17/1757 |
| | | | | 606/96 |
| 2005/0283245 A1 | 12/2005 | Gordon et al. | | |
| 2007/0016218 A1 | 1/2007 | Winslow et al. | | |
| 2007/0083203 A1 * | 4/2007 | Ribeiro | | A61B 17/92 |
| | | | | 606/279 |
| 2009/0012571 A1 * | 1/2009 | Perrow | | A61B 17/1728 |
| | | | | 606/280 |
| 2009/0036933 A1 * | 2/2009 | Dube | | A61B 17/8615 |
| | | | | 606/301 |
| 2009/0177239 A1 * | 7/2009 | Castro | | A61B 17/808 |
| | | | | 606/86 R |
| 2009/0326545 A1 * | 12/2009 | Schaffhausen | | A61B 17/8891 |
| | | | | 81/436 |
| 2010/0100138 A1 | 4/2010 | Reynolds et al. | | |
| 2011/0106087 A1 * | 5/2011 | Gamache | | A61B 17/808 |
| | | | | 606/71 |
| 2011/0252650 A1 * | 10/2011 | Veidung | | F41B 13/00 |
| | | | | 30/162 |
| 2013/0060288 A1 * | 3/2013 | Rodgers | | A61B 17/808 |
| | | | | 606/283 |
| 2015/0100094 A1 * | 4/2015 | Milz | | A61B 17/8888 |
| | | | | 606/280 |
| 2016/0106553 A1 | 4/2016 | Melkent et al. | | |
| 2016/0199073 A1 * | 7/2016 | Nino | | A61B 17/3496 |
| | | | | 606/184 |
| 2016/0310180 A1 * | 10/2016 | Prybis | | A61B 17/808 |
| 2016/0361177 A1 | 12/2016 | Biedermann et al. | | |
| 2017/0056043 A1 | 3/2017 | Jenkins et al. | | |
| 2017/0164952 A1 | 6/2017 | Nino et al. | | |
| 2017/0189204 A1 | 7/2017 | Riemhofer et al. | | |
| 2017/0239061 A1 | 8/2017 | Parry et al. | | |
| 2017/0296160 A1 | 10/2017 | O'Brien | | |
| 2017/0296288 A1 | 10/2017 | Bourque et al. | | |
| 2019/0269418 A1 * | 9/2019 | Nino | | A61B 17/3403 |
| 2020/0015870 A1 * | 1/2020 | Treace | | A61B 17/8052 |
| 2022/0183726 A1 * | 6/2022 | Genovese | | A61B 17/864 |
| 2022/0257292 A1 * | 8/2022 | Tellman | | A61B 17/90 |

FOREIGN PATENT DOCUMENTS

| | | |
|---|---|---|
| WO | 2007092441 A2 | 8/2007 |
| WO | 2010011849 A1 | 1/2010 |

\* cited by examiner

SECTION A - A

SECTION B - B

ALL IN ONE PLATE HOLDER AND SPRING LOADED AWL

CROSS-REFERENCE TO RELATED APPLICATION

This application claims the benefit of the filing date of U.S. Provisional Patent Application No. 62/894,118, filed Aug. 30, 2019, the disclosure of which is hereby incorporated by reference herein in its entirety.

BACKGROUND OF THE INVENTION

In some minimally invasive spinal surgeries, bone plates may be secured onto an outer surface of a vertebra or vertebrae of the spine as part of a complete repair. Bone plates may be used to provide supplemental fixation and to ensure that an interbody implant remains in its intended position between vertebrae by blocking a pathway out of the disc space thereby preventing backout of the interbody. This manner of usage is common in lateral lumbar interbody fusion procedures.

To secure bone plates to the spine, existing procedures tend to be cumbersome and involve multiple instruments. For example, in one known approach, a bone plate, also known as a buttress plate, is secured to a buttress plate inserter which is then used to position the bone plate on a vertebral body. Then, in a separate step, a shaft of an awl instrument is inserted through the buttress plate inserter to create a pilot hole for a bone screw to be placed through the bone plate. In other known approaches, the buttress plate inserter may be removed after placement of the bone plate, and again in a separate step, an awl instrument is inserted through the bone plate to create a pilot hole. In either of these approaches, the buttress plate inserter is removed from the bone plate prior to screw insertion into the vertebra.

Because existing approaches involve separate instruments and steps for bone plate placement and pilot hole creation for receipt of a bone plate screw, the time required to switch instruments for each step tends to lengthen the duration of the surgical procedure, which may lead to increased blood loss in a patient. Additionally, surgery of a longer duration may reduce retraction time on the nerves of the patient, which may cause leg numbness.

Thus, a need exists for improved surgical instrumentation and methods of using surgical instrumentation for the placement of bone plates on the spine.

BRIEF SUMMARY OF THE INVENTION

In a first aspect, the present disclosure relates to a system that includes a plate holder that is engageable with an awl. In one embodiment, the system is for placing a bone plate onto a bone and includes a plate holder and an awl that is releasably engaged to the plate holder. The plate holder extends from a first end to a second end and includes an engagement feature at the second end. The engagement feature is engageable with the bone plate. The awl includes a locking mechanism adjustable from a first setting to a second setting and a tip. When the locking mechanism is in the first setting, the awl is fixed relative to the plate holder and the tip is disposed within the plate holder. When the locking mechanism is in the second setting, the awl is axially translatable relative to the plate holder such that the tip of the awl is extendable out of the second end of the plate holder. In some examples, the releasable engagement between the awl and the plate holder may be provided by a first engagement feature on the awl and a second engagement feature on the plate holder. The first and second engagement features may be engageable with one another and disengageable from one another. In some examples, the awl may include a shaft and a housing surrounding the shaft.

In some examples, the locking mechanism may be on the housing and include a pin. The pin may be biased in a first position when the locking mechanism is in the first setting and may be displaced from the first position into a second position such that the locking mechanism is in the second setting. Displacement into the second position may be through application of load onto the locking mechanism. In some examples, the locking mechanism may include a spring at one end of the pin to keep the locking mechanism in the first setting unless load is applied to displace the locking mechanism. In some examples, the shaft may include a slot oriented along a length of the shaft and the pin may be disposed in the slot such that when the locking mechanism is in the first setting, a ridge protruding from the pin prevents axial movement of the awl. In some examples, the ridge may be dimensioned such that when the locking mechanism is in the second setting, the ridge does not prevent axial movement of the awl. In some examples, the locking mechanism may be a button and the shaft of the awl passes through an opening through the button. In some examples, the button may rest on a locking spring disposed internally within the housing of the awl. In some examples, the button may be translatable along an axis that is orthogonal to a longitudinal axis of the shaft of the awl. In some examples, the system may also include a compression spring disposed in between the housing of the awl and the shaft of the awl. The compression spring may be centered along a longitudinal axis of the shaft such that the compression spring changes in length when the shaft moves axially relative to the plate holder.

In some examples, the awl may include a cap attached to an end of the shaft opposite the tip, the cap sized for impaction by an impaction instrument. In some examples, the plate holder may include a plate gripper and a handle that surrounds the plate gripper. In some examples, the handle of the plate holder may include an interior surface that defines a lumen of the handle, the second engagement feature disposed on the interior surface.

In another embodiment, a system includes a plate holder with a first engagement feature and an awl with a second engagement feature engaged with the first engagement feature. The plate holder includes a body that extends from a proximal end to a distal end and two arms that extend distally from the distal end. The awl includes a housing and a shaft disposed in the housing. The housing includes the second engagement feature and the shaft includes a sharp tip. When the second engagement feature is engaged to the first engagement feature, the awl device is partially disposed within the plate holder body, the shaft is axially translatable relative to the plate holder body, and the two arms of the plate holder are engageable with a bone plate. Additionally, the awl device is disengageable from and reengagable with the plate holder.

In some examples, the first engagement feature may be a protrusion on a surface of a cannulated handle that surrounds the body of the plate holder and the second engagement feature may be knurling on the housing of the awl. In some examples, when the first engagement feature is engaged with the second engagement feature, at least a portion of the housing may be external to the handle of the plate holder. In some examples, each of the two arms of the plate holder may include protrusions at respective free ends of the two arms, the protrusions facing each other. In some examples, the body of the plate holder may include slits that separate the body into two parts at the distal end, each part including one of the two arms. In some examples, the plate holder may include a sleeve surrounding a portion of the body, the sleeve being translatable along a length of the body to control a distance between the two arms.

In another aspect, the present disclosure relates to a kit that includes instrumentation and bone plates for bone plate placement onto a bone. In one embodiment, a kit includes a plate holder, an awl and a bone plate. The plate holder includes a first engagement feature and a second engagement feature. The awl includes a third engagement feature engaged with the first engagement feature. The bone plate includes a fourth engagement feature engageable with the second engagement feature. The awl includes a locked setting and an unlocked setting. The locked setting fixes the awl relative to the plate holder along a longitudinal axis of the awl. The unlocked setting allows movement of the awl relative to the plate holder along the longitudinal axis of the awl when the awl is subject to an impaction force.

In some examples, the third engagement feature of the awl may be on a housing of the awl, the housing being cannulated such that a shaft of the awl passes entirely therethrough. In some examples, the plate holder may have a length extending between two ends and the first engagement feature is located at one of the two ends. In some examples, the awl may have a length extending between two ends and the third engagement feature is located between the two ends.

In some examples, the plate holder may have a length that extends from a first end to a second end such that the first engagement feature is at the first end and the second engagement feature is at the second end. In some examples, the third engagement feature may be formed on a housing of the awl. The housing may be cannulated with a shaft of the awl disposed entirely therethrough such that the shaft extends out of the housing from two sides of the housing. In some examples, the awl may include a button adjustable to toggle the awl between the locked and unlocked settings, the shaft of the awl passing through an opening in the button. In some examples, the shaft may include a slot having a length along a longitudinal axis of the shaft, a portion of the button passing through the slot such that the length of the slot defines a range of axial translation of the shaft of the awl relative to the housing of the awl. In some examples, the kit may include a screw insertion tool with a driver sized to pass through a cannulation of the plate holder. In some examples, the kit may include a bone screw sized for engagement by the screw insertion tool.

In another aspect, the present disclosure relates to a method of placing a bone plate onto a bone surface of a patient using an instrument. In one embodiment, the method involves using an instrument that includes a plate holder and an awl engaged to the plate holder. The steps of the method include: engaging a first engagement feature of the instrument with a second engagement feature of the bone plate; positioning the bone plate on the bone surface by manipulating the instrument; applying a first impaction force onto a second end of the instrument opposite a first end of the instrument to achieve purchase of the bone plate with the bone surface, the second end remaining fixed relative to the first end during application of the first impaction force; toggling a locking mechanism on the instrument from a first setting in which a shaft of the awl is fixed relative to the plate holder to a second setting; and applying a second impaction force onto the second end of the instrument while the locking mechanism is in the second setting, the second end of the instrument temporarily moving closer to the first end of the instrument during application of the second impaction force. The shaft of the awl used in the method includes a cutting tip such that application of the second impaction force causes the cutting tip of the awl to remove bone from the bone surface.

In some examples, the method may include assembling the instrument prior to the engaging step. Assembly may involve engagement of a third engagement feature of the awl with a fourth engagement feature of the plate holder. In some examples, engaging the third engagement feature with the fourth engagement feature may involve inserting a housing of the awl into a cannulation of a handle of the plate holder. In some examples, toggling the locking mechanism from the first setting to the second setting may involve pressing and holding a button of the locking mechanism, the locking mechanism remaining in the second setting until the button is released. In some examples, applying the second impaction force may cause the shaft of the awl to move relative to the locking mechanism of the awl by an amount defined by a length of a longitudinal slot in the shaft of the awl, a pin of the locking mechanism abutting a first end of the slot prior to application of the second impaction force and abutting a second end of the slot at least momentarily during or after application of the second impaction force.

In some examples, applying the first impaction force may include applying an initial impaction force and a subsequent impaction force that is the same or different from the initial impaction force, both the initial impaction force and the subsequent impaction force being applied while the locking mechanism is in the first setting. In some examples, applying the second impaction force may include applying an initial impaction force and a subsequent impaction force that is the same or different from the initial impaction force, both the initial impaction force and the subsequent impaction force being applied while the locking mechanism is in the second setting. In some examples, the method may include disengaging the awl from the plate holder by rotating the awl relative to the plate holder.

In another aspect, the present disclosure relates to a method of assembling a dual-function instrument. In one embodiment, the method of assembly of a dual-function instrument involves: advancing a first portion of an awl into a cannulation of a plate holder; and engaging the awl with the plate holder to form the dual-function instrument, a second portion of the awl remaining external to the plate holder subsequent to engagement. When the awl is engaged with the plate holder, the plate holder is simultaneously engageable with a bone plate and a sharp tip of the awl is axially translatable out of the plate holder to chip bone material. Additionally, when a locking mechanism on the dual-function instrument is in a first setting, the awl is fixed relative to the plate holder, and when the locking mechanism is in a second setting, the awl is axially translatable relative to the plate holder.

In some examples, engaging the awl with the plate holder may involve rotation of a knurled surface on the awl into an inner surface of the cannulated plate holder, the inner surface having protrusions thereon. In some examples, advancing the awl into the cannulation of the plate holder may involve advancing a housing of the awl surrounding a shaft of the awl into the cannulation of the plate holder such that upon engagement of the awl with the plate holder, a first portion of the housing is within the cannulation of the plate holder and a second portion of the housing is external to the cannulation of the plate holder. In some examples, following advancement of the awl into the cannulation of the plate holder to form the dual-function instrument, a portion of the shaft of the awl may remain external to the cannulation of the plate holder.

BRIEF DESCRIPTION OF THE DRAWINGS

The present disclosure will be better understood on reading the following detailed description of non-limiting embodiments thereof, and on examining the accompanying drawings, in which.

DETAILED DESCRIPTION

As used herein, the term "clinician" refers to a doctor (e.g., a surgeon), a nurse, or any other care provider, and may include support personnel or indeed other users of the contemplated medical instruments, implants and/or other technology described herein.

As used herein in reference to a bone plate or an intervertebral implant, i.e., cage, the term "superior" refers to a portion of the plate or implant nearer the patient's head, while the term "inferior" refers to a portion of the plate or implant nearer the patient's feet, when the implant is implanted in an intended position and orientation. As with the terms "superior" and "inferior," the term "anterior" refers to a portion of the plate or implant nearer the front of the patient, the term "posterior" refers to a portion of the plate or implant nearer the rear of the patient, the term "medial" refers to a portion of the plate or implant nearer the mid-line of the patient, and the term "lateral" refers to a portion of the plate or implant farther away from the mid-line of the patient. Additionally, the term "leading" refers to a portion of the plate or implant that is inserted into the patient ahead of the remainder of the plate or implant while conversely, the term "trailing" refers to a portion of the plate or implant closest to an inserter instrument and is the last part of the plate or implant inserted into the patient.

In one aspect, the present disclosure relates to a combined plate holder and awl system. In one embodiment shown in FIG. 1, system 10 includes a plate holder 20 with an awl 50 disposed therein and engaged thereto. We initially turn to the plate holder 20 part of system 10.

Figure 2:
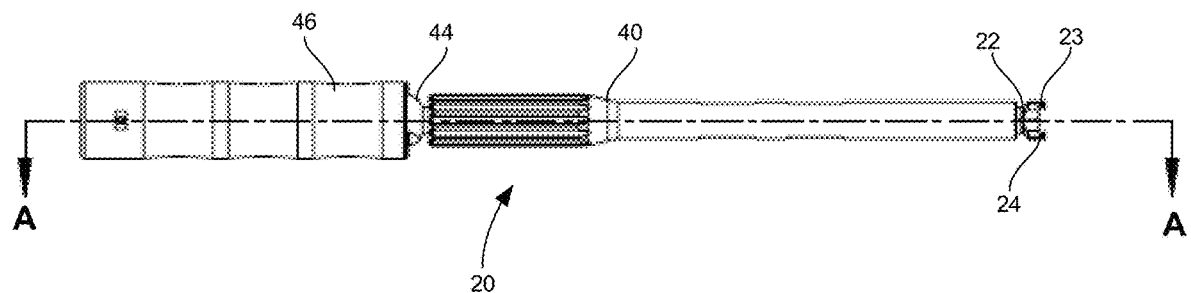
FIG. 2 is a side view of the plate holder of FIG. 1.
Figure 3:
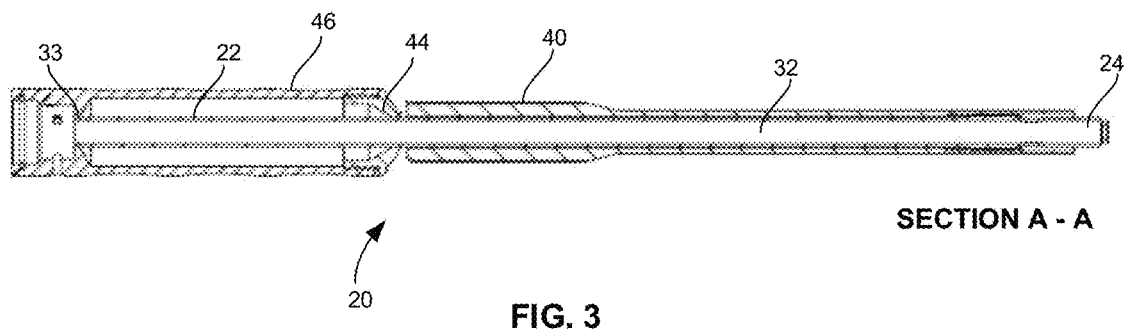
FIG. 3 is a sectional view of the plate holder of FIG. 1.

Plate holder 20 is shown in its entirety in FIGS. 2-3 and in parts in FIGS. 4-9. Plate holder 20 includes a plate gripper 22, a retention sleeve 40, a bushing 44 and a handle 46. As shown in FIGS. 2 and 3, the retention sleeve surrounds a first portion of the plate gripper while both the bushing and the handle surround the plate gripper along a second portion of the plate gripper.

Figure 7:
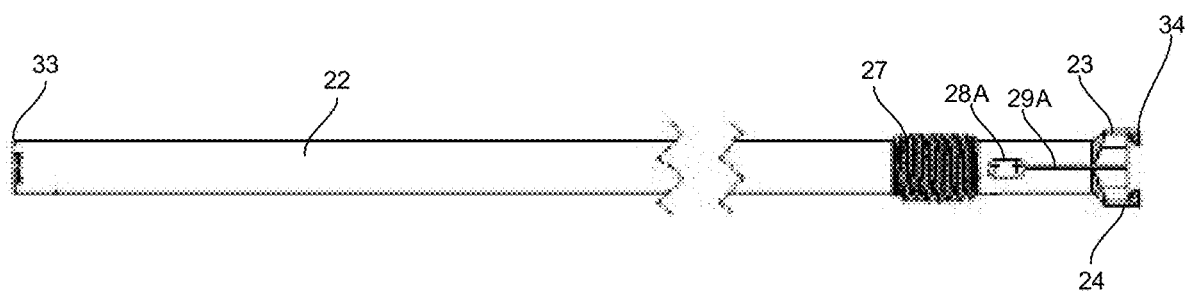
FIG. 7 is a side view of a plate gripper of the plate holder of FIG. 1.
Figure 8:
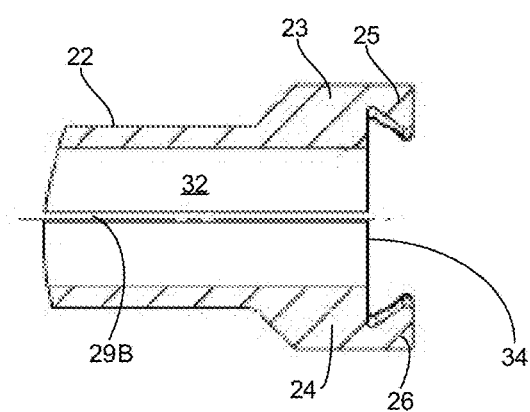
FIG. 8 is a close up partial sectional view of the plate gripper of FIG. 7.
Figure 9:
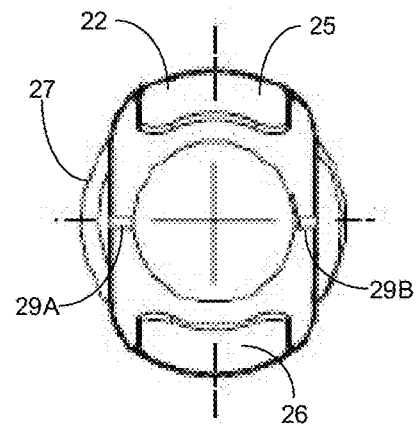
FIG. 9 is a close up front view of the plate gripper of FIG. 7.

Plate gripper 22, as shown in FIGS. 7-9, has a length that extends from a first end 33 to a second end 34. When in use, the first end is proximal to the clinician and the second end is distal to the clinician. Plate gripper 22 includes a body that is cannulated 32 throughout its length. As depicted, plate gripper is cylindrical though in alternative variations it may have other cross-sectional shapes. Adjacent to second end 34 is a threaded surface portion 27 with external threads extending around an external surface of the plate gripper. Between threaded surface portion 27 and second end 34 are a pair of slits opposite one another through a wall of plate gripper 22. Each slit includes a slit base 28A, 28B with an oblong shape, each slit base 28A, 28B extending into a slit extension 29A, 29B. Each slit base is separated from second end 34 by its respective slit extension 29A, 29B, as best shown in FIG. 7. The slits are sized and positioned so that parts of the plate gripper on opposing sides of the slits are movable with respect to each other. At second end 34, opposing parts of plate gripper 22 form arms 23, 24, as shown in FIGS. 7 and 8. Each arm 23, 24 includes an inward protrusion 25, 26 at its free end. As shown in FIG. 8, inward protrusions 25, 26 face each other.

Figure 6:
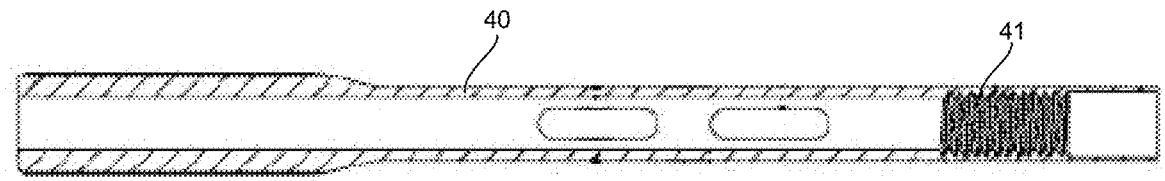
FIG. 6 is a sectional view of a retention sleeve of the plate holder of FIG. 1.

Surrounding plate gripper 22 on the first portion of the plate gripper length is retention sleeve 40, shown surrounding plate gripper in FIG. 2 and independently in FIG. 6. Retention sleeve 40 is cannulated and includes a threaded portion 41 on its inner surface. Threaded portion 41 is dimensioned so that it is engageable with threaded surface portion 27 of plate gripper 22 to lock retention sleeve 40 to plate gripper 40. Further, through the inclusion of a thread-type connection, an axial position of retention sleeve 40 relative to plate gripper 22 is adjustable through rotation of retention sleeve 40 relative to plate gripper 22. The relationship between the retention sleeve and the plate gripper is such that advancement of retention sleeve towards arms 23, 24 causes arms to move toward one another and withdrawal of retention sleeve away from arms 23, 24 causes arms to move apart until the arms reach a neutral, unloaded position.

Figure 5:
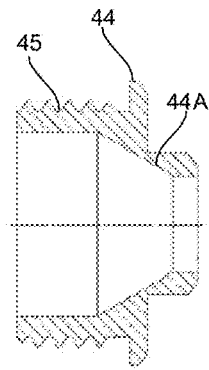
FIG. 5 is a sectional view of a bushing of the plate holder of FIG. 1.

Between a position of retention sleeve 40 secured to plate gripper 22 and first end 33 of plate gripper 22 are handle 46 and bushing 44. Both the plate gripper and the handle are cannulated and each surrounds plate gripper 22. Bushing 44, shown in isolation in FIG. 5, is fixedly secured to plate gripper 22, as shown in FIG. 3. Fixation of bushing 44 to plate gripper 22 may be through a weld at an end of the bushing facing second end 34 of plate gripper 22. In turn, handle 46 is fixed to bushing 44 via internal threads 47 of handle 47 that are engaged with external threads 45 of bushing 44. As additional securement, first end 33 of plate gripper 22 may be fixed to handle 46 directly. Such fixation may be in the form of a weld at the first end of the plate gripper.

Figure 4:
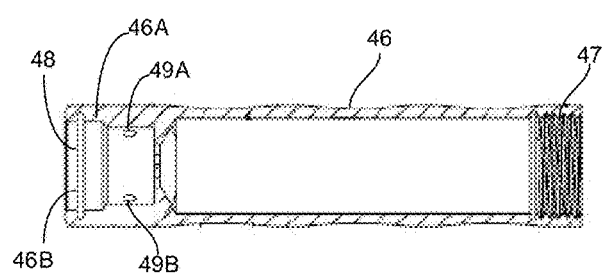
FIG. 4 is a sectional view of a handle of the plate holder of FIG. 1.

As shown in FIG. 4, an interior surface of handle 46 includes various engagement features. In particular, disposed on a groove 46B on the inner surface of handle 46 at its trailing end adjacent to first end 33 of the plate gripper is a circumferential retaining ring 48. Retaining ring 48 fits loosely within groove 46B when no structures are disposed within handle 46. Additionally, further from the trailing end of the handle than the groove are a plurality of pins extending radially inward from the interior surface and spaced apart from one another. The depicted embodiment includes three pins, two of these, pins 49A, 49B, being shown in FIG. 4. The pins are fixed relative to handle 46 with fixation by weld, for example. As described in greater detail below, the retaining ring and pin features provide one exemplary means of releasable fixation of the awl to the plate holder. It should be appreciated, however, that alternative engagement features for the complementary awl and handle, such as protrusions and/or recesses of various arrangements, are also contemplated.

Figure 10:
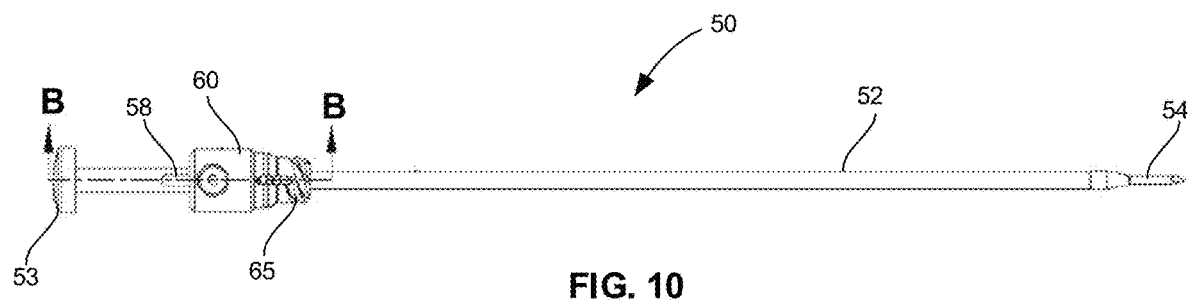
FIG. 10 is a side view of the awl of FIG. 1.
Figure 12:
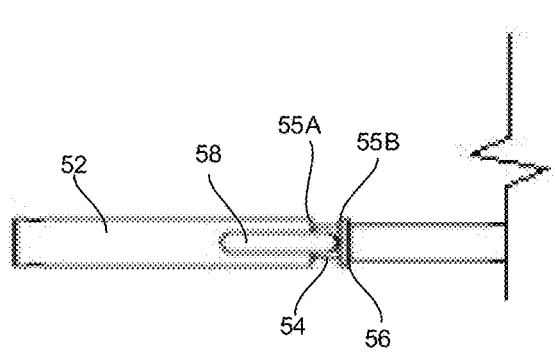
FIG. 12 is a close up partial side view of a shaft of the awl of FIG. 10.

Turning now to the awl of system 10, awl 50 is best shown in FIG. 10. Awl 50 includes shaft 52 and housing 60 that surrounds and encloses a portion of shaft 52. Shaft 52 of awl 50 extends from a cap 53 attached to the shaft at a first end and a tip 54 at a second end. Although cap 53 is shown having a particular shape and size, it is contemplated that in variations the cap may be any shape that allows for receipt of impaction forces. Tip 54 includes a cutting feature. The cutting feature is shaped for cutting bone, but in alternative variations, may be adapted for other functions. Awl shaft 52 has a generally uniform shape over most of its length, although adjacent to cap 53, includes several structural features for interaction with housing 60. In particular, and as shown in FIG. 12, closest to the first end of the awl is a longitudinally extending slot 58 through shaft 52. Slot 58 forms a path entirely through shaft 52 such that an element may be disposed through a full depth of the shaft in a direction orthogonal to a length of shaft, as described in detail elsewhere in the disclosure with respect to pin 77. Shaft 52 also includes a recessed portion 54 located over an end portion of slot 58. An overall sectional size of shaft 52 in recessed portion 54 is smaller than on adjacent surfaces of the shaft, as shown in FIG. 12. Recessed portion 54 extends from a first end 55A to a second end 55B. Slot 58 is positioned so that one end of slot 58 is within recess 54 while an opposite end extends past first end 55A. Shaft 52 includes a circumferential protrusion 56 at second end 55B of recess 54.

Figure 11:
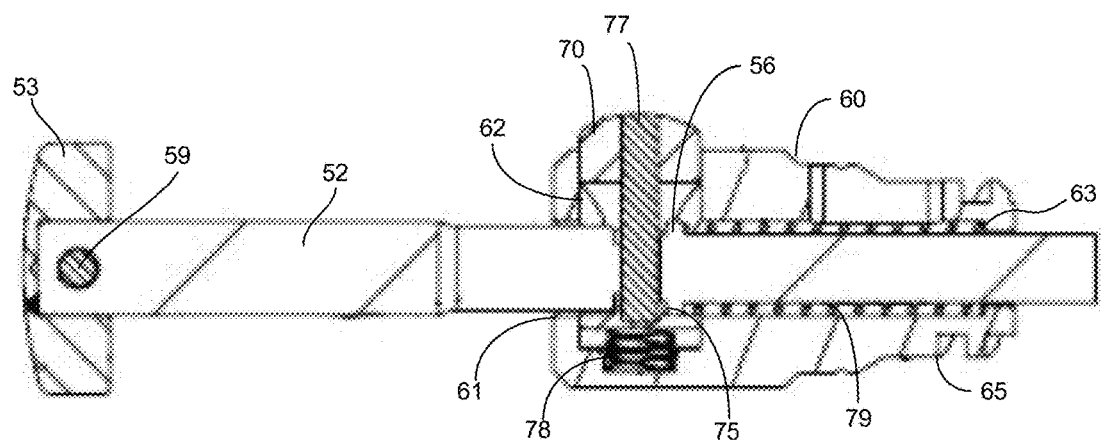
FIG. 11 is a close up partial sectional view of the awl of FIG. 13.

Housing 60 of awl 50 is best shown in FIG. 11. Housing 60 includes a longitudinal passageway 61 for the disposal of awl shaft 52, a cavity 62 that is transverse to longitudinal passageway 61, and an engagement feature 65 on its external surface distal to cap 53. In one example, and as shown, engagement feature 65 is in the form of a knurled surface with features sized and shaped for engagement with inner surface 46A of housing 46. In some examples, the housing includes an engagement feature with a triple lead groove and is used with a handle that has pins positioned in a complementary manner. In other examples, the engagement feature may be helical threads. Longitudinal passageway 61 includes shoulder 63 adjacent to a leading end of housing 60 such that a portion of longitudinal passageway between shoulder 63 and a leading end of housing 60 is narrower than a remainder of the passageway, as shown in FIG. 11. With awl shaft 52 and longitudinal spring 79 disposed in longitudinal passageway 61, longitudinal spring 79 surrounds awl shaft 52 and is held in place by circumferential protrusion 56 at one end and shoulder 63 at an opposite end. In the depicted embodiment, no additional elements are required to hold spring 79 in place within housing 60.

Turning to the elements within cavity 62 of housing, a locking spring 78 is positioned at a base of cavity 62 as shown in FIG. 11. In some examples, including for awl 50 shown in FIG. 11, awl housing 60 may include a cleaning slot that provides access to locking spring 78 from knurled surface 65. Immediately adjacent to locking spring 78 within cavity 60 and resting on spring 78 is button 70, shown in isolation in FIG. 13. Button 70 includes a pin 77 disposed therein, as shown in FIG. 11. The locking spring, button and pin are one example of a locking mechanism. Pin 77 is fixed relative to button 70. In some examples, fixation may be in the form of a weld. Additionally, button 70 includes a transverse passageway 72 that defines an enclosed path parallel to a longitudinal axis of the awl shaft when button 70 is disposed within cavity 62. At a base of through passageway 72 is locking ridge 75 which encloses a void that defines a seat 74 therein. Aligned with the seat and orthogonal to through passageway 72 is pin opening 73, extending from an outer surface of button 70 to through passageway 72. Pin opening 73 and seat 74 are sized and positioned so that pin 77, a generally linear structure, is disposed within both when installed in button 70, as shown in FIG. 11. Moreover, when pin 77 is disposed in button 70, a base of pin 77 is surrounded by locking ridge 75. Slot 58 of shaft 52 has a width marginally wider than a diameter of pin 77. In this manner, when locking ridge 75 is within recess 54 and aligned with circumferential protrusion 56, as shown in FIG. 11, shaft 52 is prevented from moving axially by such alignment. However, when button 70 is depressed and locking ridge 75 is entirely out of a path of translation of awl shaft 52, i.e., below the shaft in the awl orientation shown in FIG. 11, slot 58 is axially translatable relative to pin 77. This is described in greater detail in the method of use.

Figure 1:
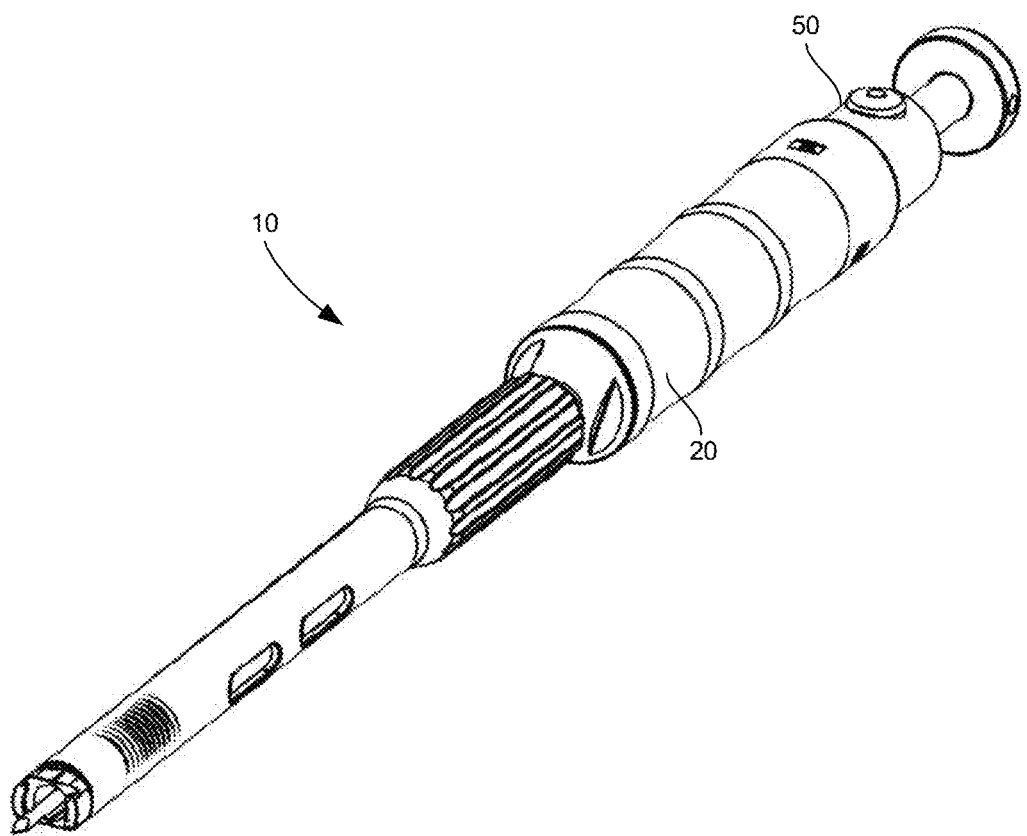
FIG. 1 is a perspective view of a combined plate holder and awl system according to one embodiment of the disclosure.
Figure 15:
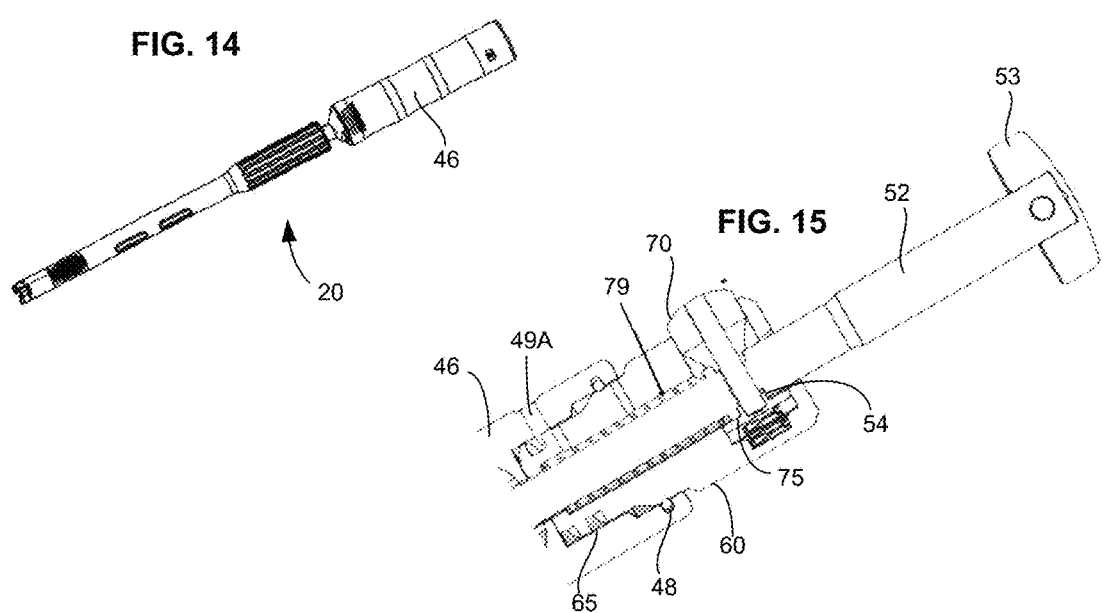

Combining plate holder 20 with awl 50, components described in detail above, produces system 10, as shown in FIG. 1. Through connection of the plate holder and the awl, the system becomes a single all-in-one structure. FIG. 15 illustrates the location of interconnection between the elements. In particular, engagement feature 65 of housing 60 is engaged to the inner surface of handle 46, thereby creating a releasably fixed connection between the elements. In the embodiment shown, engagement is based on rotational engagement between engagement feature 65 and inner surface 46A of housing. A fixed relationship between the awl and the bone plate holder is established when retaining ring 48 is compressed on an outer surface of housing 60 and pins 49A-C (not all shown) project from inner surface 46A into recessed surfaces of the knurled surface of engagement feature 65. The above described fixation is not irreversible and the awl may be disengaged by rotation of the awl relative to the plate holder in a direction opposite to that used for engagement.

With the plate holder 20 and awl 50 fixed to one another as described above, system 10 is usable as a single unit during surgery and does not require separate placement of each instrument into the surgical site or any other two step process. When awl 50 is fixed to plate holder 20, button 70 remains actuatable to control whether the awl is locked or unlocked relative to plate holder 20, i.e., to control whether the awl may translate axially upon application of force to cap 53. Further, in addition to the functions of the awl, the arms of the plate holder remain usable in the combined system. In particular, the arms may be used to engage with an implant, such as a bone plate, for example. In these respects, the system 10 when assembled is a dual-function instrument and is advantageous in that it combines two instruments into a single instrument, thereby eliminating the need to switch instruments to perform the bone plate placement and cutting function of the awl. Greater detail regarding the functional features of the system is provided elsewhere in the disclosure in the description of the methods of use.

Although described together as part of system 10, it should be appreciated that the present disclosure also contemplates embodiments directed to singular structures of the system such as the plate holder, for example.

The plate holder may be varied in many ways. In some examples, the retention sleeve may be non-rotatably engaged to the plate gripper. For example, the retention sleeve may engaged with the plate gripper so that the retention sleeve may be shifted longitudinally without rotation to axially translate the retention sleeve along the plate gripper from a first position to a second position thereby changing the spacing between the arms of the plate gripper. In these examples, the engagement feature may be on an internal surface of the retention sleeve and may be sized to engage with a complementary feature on an external surface of the plate gripper. In some examples, the connection between the retention sleeve and the plate gripper may be snap fit. In another example, the plate holder may have no retention sleeve at all. Instead, the arms at the distal end of the plate gripper may be biased in a closed position and include tapered tips so that upon contact with a plate, the arms may spread apart and then snap into place once disposed within recesses of a bone plate. In other examples, the arms may include outward facing protrusions at their respective free ends. In some examples, the arms may include engagement features facing distally from respective free ends of the arms. In either of these variations, a bone plate to be engaged may have recesses on its surface to complement the engagement features of the arms. In still further examples, the shape of the protrusions, in an applicable direction from the arms, may be any shape suitable to engage with a complementary feature on a bone plate to be engaged. In other examples, the arms may be shaped to engage with implants other than bone plates.

The awl may be varied in many ways. In some examples, the longitudinal spring and/or the locking spring within the awl housing may be a biasing element that is not a spring. In some examples, the axially translatable button, i.e., push-button, may be substituted with a rotatable knob to control whether the awl is in the locked or unlocked position. The knob may include a pin that passes through a slot in the shaft of the awl, as with the depicted embodiment, and may include a threaded engagement with a base outside of the shaft. The pin may include a wider section that is aligned with the awl shaft in the locked position while being out of alignment with the awl shaft in the unlocked position, the change in position being obtained through rotation of the knob. In this manner, the wider section performs a function similar to that of locking ridge in button 70. In still other examples, a setting of the button, i.e., locked or unlocked, in the awl housing may be controlled electronically via a touch screen or other similar means.

Finally, the overall system may be varied in many ways. In some examples, the engagement between the plate holder and the awl may be snap fit so that the awl may be inserted into the opening in the handle of the plate holder in a linear manner. For instance, the plate holder and the awl may include complementary ball and detent components. In some examples, the engagement between the plate holder and the awl may be through an interference fit. For instance, an outer surface of the awl housing may be formed from an elastic material that may be compressed upon advancement into the cannulation of the plate holder housing, and upon release once disposed in the housing, may expand to form a fixed engagement between the awl and the plate holder. In still other examples, the housing of the awl may include an outer wall (outer portion) spaced apart from and enclosing an inner portion of the housing holding the longitudinal spring such that the outer wall is sized to fit around an outer surface of the plate holder handle. In these examples, engagement features on an inner surface of the outer wall are engageable with complementary engagement features on an outer surface of the plate holder handle. When engaged with one another, the circumferential handle structure is disposed in between the outer portion and the inner portion of the awl housing. In some examples, the awl housing may be uniform in size along its length from a leading end to a trailing end. In other examples, the awl housing may have a reverse taper. In these variations, the inner surface of the handle is shaped to complement the shape of the awl housing.

In yet another example, the housing of the awl may be built into the plate holder structure. In particular, each feature of the awl housing, including the longitudinal spring and the button, may be built into the handle of the plate holder. Thus, the only structure engaged to and removed from the plate holder is the awl shaft. With this configuration, the pin of the button is removed in order to place the awl shaft into the plate holder. Then, with the awl disposed in the plate holder, the pin is placed back into engagement with the button to engage the awl to the plate holder. Similarly, to remove the awl from the plate holder, the pin is removed from the button. Thus, the pin may be removably engaged to the button to allow for removal of the awl shaft from the remainder of the system and for engagement of the awl shaft to the remainder of the system.

In another aspect, the dual-function instrument and/or its parts as contemplated herein may be included as part of a kit. In some embodiments, a kit includes an awl and a plate holder. In some embodiments a kit includes an awl, a plate holder and a bone plate. In other embodiments, a kit includes two or more of at least one of an awl, a plate holder and a bone plate. Thus, a kit may include five awls, five plate holders and five bone plates. Another kit may include two awls and two plate holders. In yet another example, a kit may include one awl, one plate holder, and ten bone plates. In another embodiment, a kit may include at least two sizes and/or types of bone plates. In some examples, the kit is limited to including bone plates, while in other examples, the variety of bone plates may be accompanied by one or more awls and plate holders. It should be appreciated that the above embodiments are illustrative and that any combination of the above components may be used to form a kit.

In some embodiments, a kit includes an awl, a plate holder and one or more additional surgical instruments, such as instruments used for spinal access in spinal surgery. For example, a kit may include an awl, a plate holder and one or more of a retractor, a driver, a tool to actuate a locking cover on a bone plate, modular instrument handles, screws, implants, and other related components.

The kit may be varied in many ways. For example, the various combinations of elements of any kit contemplated herein may be included in a single package or distributed among multiple packages. In other examples, the kit contemplated herein may be accompanied by an instruction manual on how to perform one or more of the methods of using the contents of the kit.

Figure 14:
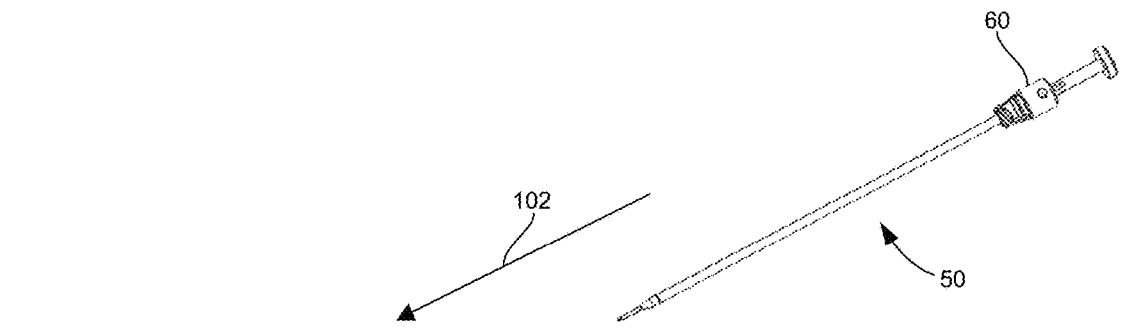
FIGS. 14-19, 20A-20B and 21A-21B are steps in a method of using a combined plate holder and awl system according to another embodiment of the disclosure.

In another aspect, the present disclosure relates to a method of assembling an awl 50 with a plate holder 20. It should be appreciated that the assembly of the awl with the plate holder may also be an initial step in a method of using system 10 to fix a bone plate onto a bone, as described separately below. Turning to the details of the assembly process, in one embodiment, shaft 52 of awl 50 is advanced through cannulation 32 of plate gripper 22 until housing 60 of awl 50 contacts inner surface 46A of handle 46. This step commences from a position such as that shown in FIG. 14, where advancement of the awl is denoted by reference numeral 102. Once housing 60 is in contact with the inner surface of handle 46, awl 50 is rotated about its longitudinal axis and relative to plate holder 20 to rotate housing 60 into an interior of handle 46 and thereby engage the awl with the plate holder to form a fixed connection. In particular, the groove of knurling 65 on the outer surface of housing 60 engages with pins 49A-C protruding from inner surface 46A of housing 46 so that each pin sits within the groove as the awl is rotated relative to the housing. Additionally, once the housing approaches its fully inserted position within the handle through the threading of the housing into the handle, retaining ring 48, also on inner surface 46A of housing 46, presses against an outer surface of awl housing 60 to form an interference fit between the retaining ring and the awl housing. In some examples, the outer surface of the awl housing at its trailing end may have a groove for receipt of the retaining ring. When the awl housing includes a groove or other engagement feature for the retaining ring, an audible snap is heard along with tactile feedback to the clinician when the retaining ring moves into place in the groove. One advantage of the retaining ring is that it prevents loosening of the awl from the plate holder. Assembly is complete when awl 50 is fixed to plate holder 20, as shown in FIG. 15. The engagement between the awl and the plate holder is sometimes referred to herein as releasable or detachable because although the awl and plate holder are integrated with one another once assembled, they may also be separated again at a later time. In the above described embodiment, for example, such disassembly involves rotating the awl relative to the plate holder in a direction opposite to that used for assembly.

In some embodiments, a method of assembly involves assembly of the awl. For example, with awl housing 60, assembly commences with insertion of locking spring 78 into a base of cavity 62, as shown in FIG. 11. Button 70 is then inserted through cavity 62 so that button 70 rests directly over locking spring 78. With button 70 in position within housing 60, longitudinal spring 79 is advanced through longitudinal passageway 61 and through passageway 72 of button 70 until it abuts shoulder 63. Next, awl shaft 52 is advanced through longitudinal passageway 61 until slot 58 of shaft 52 is aligned with button 70. Then, pin 77 is inserted through pin opening 73 of button, through slot 58 of shaft 52, and finally into seat 74. Pin 77 may then be welded into place onto button 70, a final secured position being shown again in FIG. 11. Substitutes for welding are also contemplated. Cap 53 may be secured to shaft 52 at any time during assembly. To secure cap 53 to shaft 52, a pin 59 may be welded in place to make the connection between the elements, though any other form of fixation may also be used.

In some embodiments, a method of assembly involves assembly of the plate holder. For example, and as shown in FIG. 4, retaining ring 48 is snapped into groove 46B on inner surface 46A of handle 46. Pins 49A-C (not all shown) are then placed onto openings in handle 46 and secured into place. Securement may be in the form of a weld. Bushing 44 is then rotated into engagement with handle 46 via complementary threads: Threads 45 on the outer surface of bushing 46 engaging with threads 47 on inner surface 46A of handle 46. In some variations, a medical grade thread lock may be applied to the threads of the bushing to promote locking when the elements are rotatably engaged. Retention sleeve 40 is then advanced relative to plate gripper 22 through rotation of retention sleeve 40 about its axis over plate gripper 22 until inner threads 41 of retention sleeve 40 are axially aligned with threaded surface portion 27 on plate gripper 22 and part of retention sleeve 40 is distal to threaded surface portion 27. Combined handle 46 and bushing 44 are then slid over plate gripper 22 on a proximal side of plate gripper 22. Retention sleeve 40 and handle 46 are shown positioned on plate gripper 22 in FIG. 2. Handle 46, when properly positioned on plate gripper 22, is then fixed to the plate gripper. In some examples, fixation may be via welds between bushing 44 and plate gripper 22 and between plate gripper 22 and handle 46 at a proximal end of plate gripper 22.

In another aspect, the present disclosure relates to a method of using the awl and plate holder system to secure a bone plate to a bone and to create a pilot hole in the bone for a screw to be placed through the bone plate. In the described embodiments, the method is described with respect to a bone plate placed minimally invasively onto the spine of a patient. However, it is envisioned that the instruments of the embodiments of the present disclosure may be used in other areas of the body.

Figure 16:
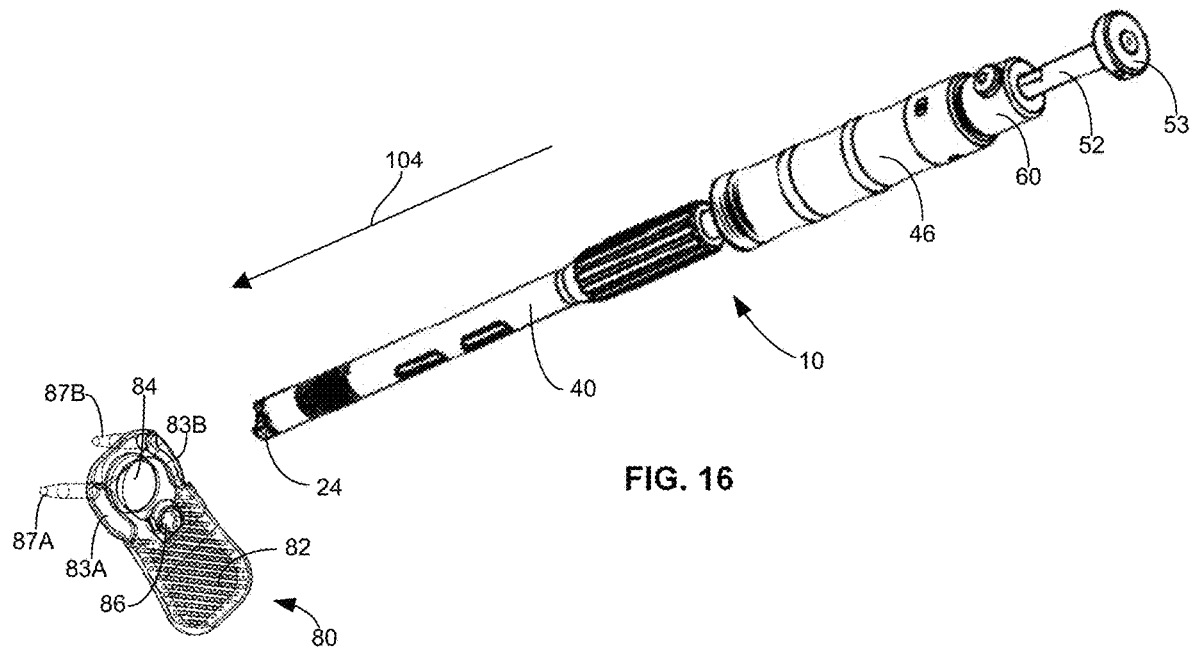
Figure 17:
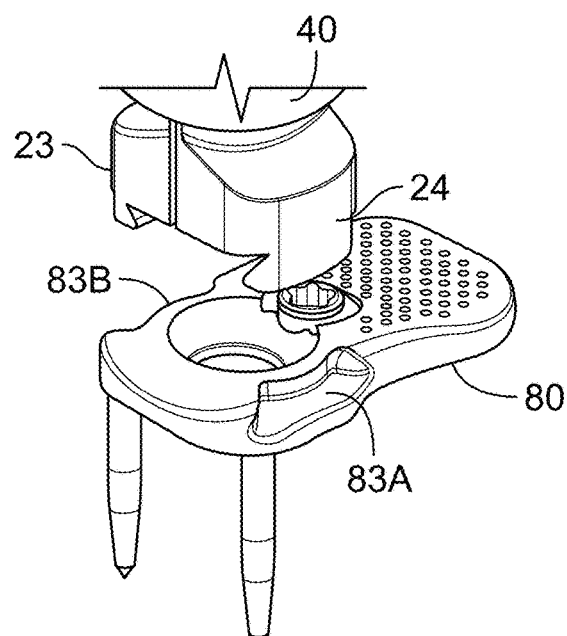
Figure 18:
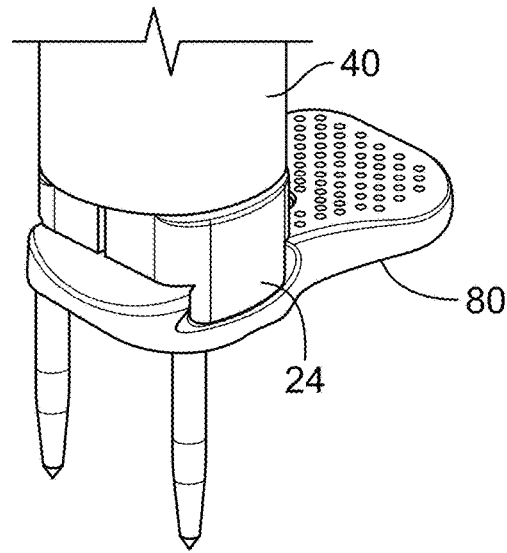

In one embodiment, a method involves the use of system 10 and begins with awl 50 already fixed to plate holder 20, as shown in FIGS. 15 and 16. In a variation of this method, the method may commence with an additional initial step involving assembly of awl 50 and plate holder 20 as described above and shown in FIGS. 14-15. With system 10 in an assembled state, retention sleeve 40 is checked to verify that it is rotated counterclockwise (or clockwise with a reverse thread) so that it is withdrawn sufficiently from arms 23, 24 so that arms 23, 24 are in an open, or spread apart position. System 10 is then advanced onto bone plate 80 as denoted by reference numeral 104 and shown in FIG. 16. Bone plate 80 includes a trailing surface 82 that faces away from bone when secured onto a bone surface. Within trailing surface are recesses 83A, 83B on lateral sides of the bone plate, an aperture 84 through the bone plate in between the recesses, and a locking element 86 adjacent to the aperture. As shown in FIG. 17, arms 23, 24 of plate gripper 22 of system 10 are advanced toward and into recesses 83A, 83B. Although arms 23, 24 are shown at a particular spacing in FIG. 17, it should be appreciated that the arms may be further apart and retention sleeve 40 further withdrawn toward the clinician during performance of this step than is shown in FIG. 17. Once the arms are in a position within the recesses, retention sleeve 40 is rotated clockwise to axially advance retention sleeve 40 over the arms to bring the arms together into a closed position, as shown in FIG. 18. This grips the arms of the plate gripper onto bone plate 80.

It should be appreciated that in alternative arrangements, the retention sleeve of the plate holder may operate differently than described above to control whether the arms of the plate gripper are in an open or closed position. For example, the retention sleeve may slide along the plate gripper in an axial movement, rather than through a rotational movement about its axis.

Once plate holder 20 is engaged with bone plate 80, the combined elements are ready for passage through a surgical portal to a target site on the spine of the patient. At this time, or at any time prior to reaching this step, a surgical access portal into the spine of the patient is prepared (not shown). Preparation of a surgical access portal may be accomplished through the use of a retractor, such as the retractors described in any one of U.S. Pat. Nos. 8,449,463, 9,675,337, and 10,405,842 and in U.S. Pat. App. Pub. No. 2017/0296160, the disclosures of which are hereby incorporated by reference herein in their entirety. Of course, other established methods of retraction to create a surgical portal for access may also be employed. Then, in some examples, material of disc 3 may be removed so that an intervertebral implant 6 may be implanted into the intervertebral space.

Figure 19:
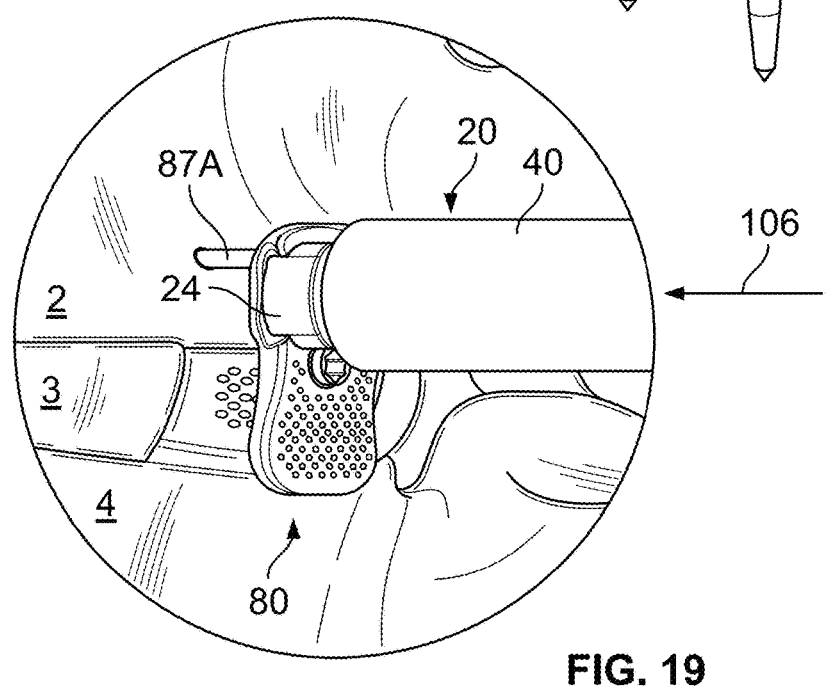

With a surgical access portal created and a target site for bone plate placement accessible, and in some cases, an implant 6 being implanted into the intervertebral space, system 10 with bone plate 80 attached is advanced through the access portal and onto vertebral body 2 of the spine as denoted by reference numeral 106. As shown in FIG. 19, fangs 87A, 87B of bone plate 80 are pushed through vertebral body 2 to prevent any rotation of bone plate 80 during subsequent steps of the method. To push the fangs into the bone, or to aid in pushing the fangs into the bone, a mallet may be applied to cap 53 of the awl component of the system. Because the awl will be in the locked position at this time by virtue of button 70 being in its biased position, i.e., the awl is locked relative to the plate holder, the force applied to the system by the mallet will go directly into bone plate 80. In this manner, the clinician is able to control the force applied to the plate based on the force applied to the awl cap by the mallet. Of course, in a variation of this step, another impaction tool may also be used in place of a mallet.

When it is established that the bone plate is satisfactorily held in place on the bone, the next step involves preparation of a pilot hole in the bone for insertion of a screw. During the previous step, awl 50 was in its locked position, and tip 54 of awl 50 was disposed entirely within an interior channel (cannulation 32) of the plate gripper. In this manner, while the system 10 is used as an impaction device, the awl does not project out of the plate holder and impact any external surfaces. However, once bone plate 80 is satisfactorily held on the surface of vertebral body 2 via fangs 87A, 87B, button 70 may be toggled, i.e., actuated, to commence use of the awl component of system 10 for the creation of a hole in the bone for screw placement through the bone plate. Thus, from a first setting where the button is not loaded, the button is moved to a second setting by applying load to hold it in a displaced position.

Figure 13:
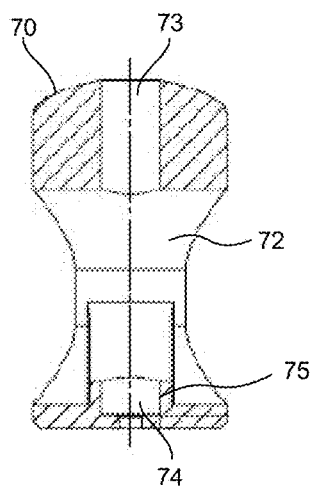
FIG. 13 is a sectional view of a button of the awl of FIG. 10.
Figure 20A:
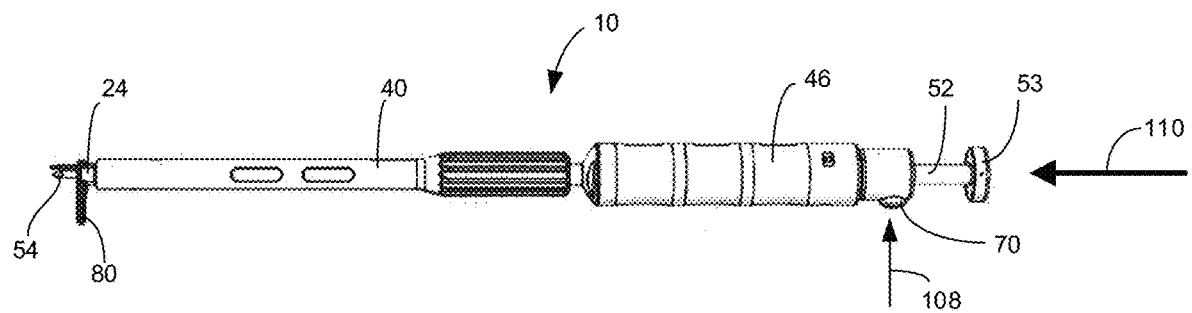
Figure 20B:
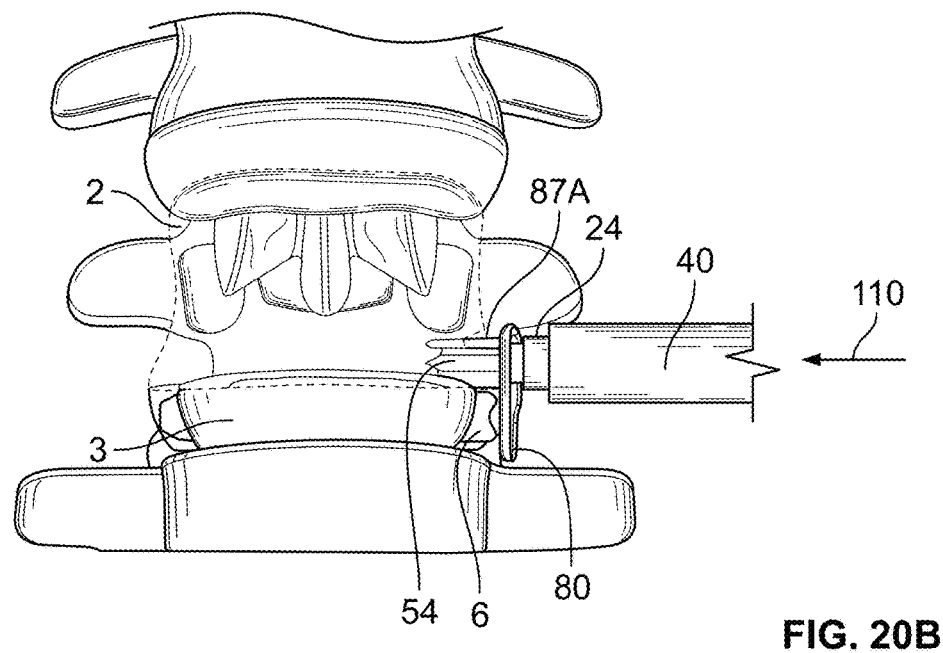

When the clinician depresses button 70 as indicated by reference numeral 108 in FIG. 20A, awl shaft 52 becomes unlocked relative to plate holder 20 so that shaft 52 is axially translatable within plate holder 20 as long as button 70 is depressed. In terms of mechanics, FIGS. 11-13 illustrate the details of the awl locking mechanism including the features that provide for the locked and unlocked settings. As button 70 is depressed within housing 60, locking ridge 75 of button 70 moves out of recess 54 on shaft 52, and thus out of the path of shaft 52. When locking ridge 75 is out of the path of shaft 52, the only structure restraining axial movement of shaft 52 is pin 77, as opposed to pin 77 and locking ridge 75. In this setting while button 70 remains depressed, shaft 52 is free to slide relative to pin 77 over a length of slot 58. Thus, impaction forces applied to cap 53 advance tip 54 of shaft 52 out of plate holder 20, as shown in FIGS. 20A and 20B. Reference numeral 110 indicates the direction of impaction force applied to system 10.

Thus, to create a hole for screw placement through bone plate 80, button 70 is held in a depressed position and cap 53 is impacted as indicated by reference numeral 110. The application of an impaction force on cap 53 causes shaft 52 to advance through housing 60 and relative to plate holder 20. In doing so, longitudinal spring 79 compresses to control the displacement of shaft 52. After each impact, longitudinal spring 79 expands and awl 50 returns to its biased position where tip 54 rests within the cannulated portion of plate gripper 22, and the process is repeated. A clinician may perform any number of impactions to create a desired pilot hole in the bone for screw placement. During this step, arms 23, 24 of plate holder 20 remain engaged to bone plate 80 and thus plate holder 20 and awl 50 are not only engaged to one another as part of system 10, but are serving simultaneous functions: The plate holder maintaining alignment of the system with the bone plate, and the awl creating the hole aligned with aperture 84 for screw placement. Through the described procedure, one advantage, particularly when the procedure is employed in minimally invasive procedures such as lateral lumbar interbody fusion, is the significantly reduced duration required to position and prepare the bone plate relative to existing procedures where separate steps are required for bone plate placement and pilot hole creation. Thus, potential blood loss is reduced and the duration the nerves are subject to retraction time is also reduced. Returning to the method, once the pilot hole is deemed satisfactory, the bone plate is ready to receive a screw that will be inserted into the pilot hole.

Figure 21A:
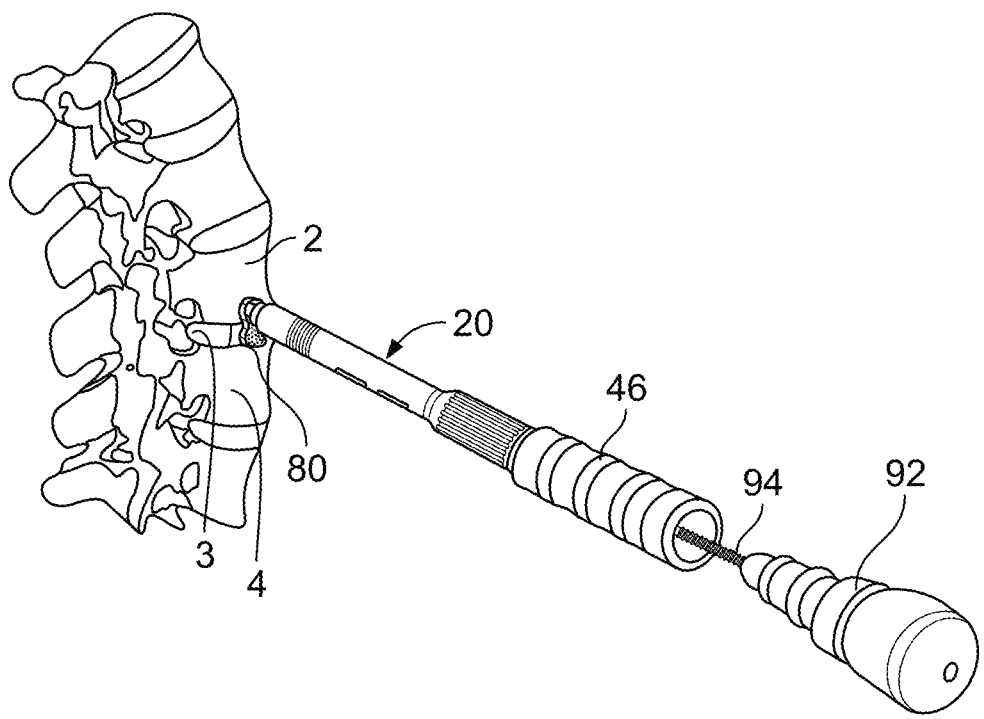
Figure 21B:
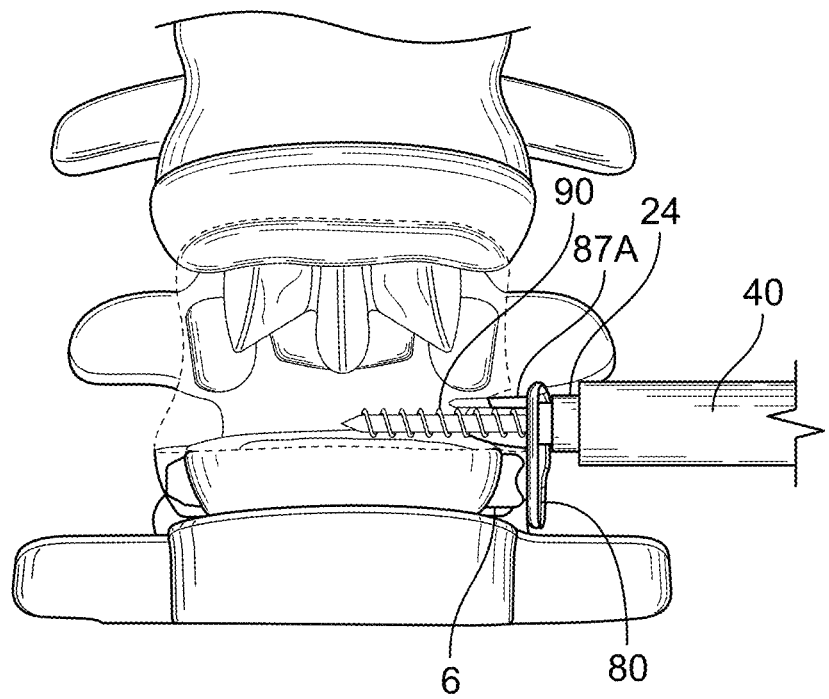

The screw placement step may be performed in a variety of ways, as will now be described in greater detail. In some embodiments, the awl is detached from the plate holder by rotating the awl housing out of the handle. Then, with plate holder 20 still engaged to bone plate 80, a handle 92, a driver 94 attached to the handle, and a holding screw 90 attached to the driver, are advanced into plate holder 20, as shown in FIGS. 21A and 21B. The pathway through cannulation 32 of plate gripper 22 is sufficiently sized so that driver 94 is advanceable therethrough. Screw 90 is inserted through aperture 84 in plate 80 and then rotated into place within the pilot hole formed in vertebra 2. This technique is particularly suitable when screw 90 is intended to be inserted perpendicular to the bone plate, as shown in FIG. 21B.

In other embodiments, the entire system 10 is removed from bone plate 80 after the hole is formed in vertebrae 2, and screw is inserted into the pilot hole. When the surgery calls for insertion of the screw at an acute angle relative to the bone plate, an anti-torque handle may be placed on the bone plate prior to driving in the screw (not shown). The anti-torque handle is attached to the bone plate in a manner that prevents rotation of the bone plate during insertion of the screw. In these embodiments, it is contemplated that the screw may be placed at any desired angle relative to the vertebral end plate from 0 degrees to 25 degrees. In still further embodiments, the screw may be inserted with a screw insertion tool without any additional supporting instruments affixed to the bone plate.

Once screw 90 is securely in place in the vertebra, a driver is retrieved with a drive element that complements the drive element of locking element 86 of bone plate 80. Locking element 86 is shown as part of bone plate 80 in FIG. 16. By engaging and rotating locking element 86, locking element 86 rotates to block screw 90 from back out and thereby prevent it from dislodging from vertebra 2 (not shown). In embodiments where the bone plate does not include a locking element for blocking a screw, this step is not performed. The bone plate placement is final at this point in the procedure and any remaining tools are removed from the surgical site. Procedures are then chosen by the clinician to close the surgical access portal and the wound.

The method of using system 10 and its components may be varied in many ways. For instance, in one example, plate holder 20 may be engaged to bone plate 80 prior to engagement of awl 50 to plate holder 20. In this manner, awl 50 may subsequently be engaged to plate holder 20 either before or after plate holder 20 is advanced to the surgical site. Engagement between the plate holder and the bone plate, along with engagement between the awl and the plate holder, may be as described for the embodiment depicted in FIGS. 14 through 20B.

In other examples, plate holder 20 may be used independently in a method of placing a bone plate on a bone. The method may involve engagement of the plate holder to the bone plate, followed by advancement of the bone plate to a desired engagement surface on the spine. The plate holder may be engaged to the bone plate in the manner described for the embodiment depicted in FIGS. 14 through 20B. For application of impaction forces, an impaction tool may be applied to a proximal end of the handle of the plate holder in the absence of the awl.

In still further examples, the methods of using system 10 may be employed to place implants other than bone plate 80. In some examples, implants may be other bone plates. In still further examples, other types of implants may be held by the plate holder and positioned for the creation of a pilot hole through an aperture of the implant. Provided that the implant has recesses that may be engaged by the arms of the plate holder, and provided that an aperture of the implant is positioned on the implant so that the awl may advance therethrough, the plate holder and awl system may be used with such implants.

It should be noted that any of the instruments and methods disclosed herein may be used in conjunction with robotic technology. For example, any of the instruments described herein may be used with robotic surgical systems to place a bone plate or screw in a patient. The bone plate or screw may be manipulated with a robotic system or a robotic arm to rotate or position the bone plate or screw, and/or to anchor the screw through the bone plate during a procedure. Further, any or all of the steps described in the methods for performing a bone plate placement procedure of the present disclosure may be performed using a robotic system.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A system for placing a bone plate onto a bone comprising:
   a plate holder extending from a first end to a second end opposite the first end, the plate holder including an engagement feature at the second end, the engagement feature engageable with the bone plate; and
   an awl releasably engaged to the plate holder, the awl having a length extending to a tip and including a locking mechanism adjustable from a first setting to a second setting,
   wherein when the locking mechanism is in the first setting, the awl is fixed relative to the plate holder and the tip of the awl is disposed entirely within the plate holder such that the second end of the plate holder is further from the first end of the plate holder than the tip,
   wherein when the locking mechanism is in the second setting, the awl is axially translatable relative to the plate holder such that the tip of the awl is extendable out of the second end of the plate holder, and
   wherein the adjustment of the locking mechanism between the first setting and the second setting is independent of the axial translation of the awl.

2. The system of claim 1, wherein the releasable engagement between the awl and the plate holder is provided by a first engagement feature on the awl and a second engagement feature on the plate holder, the first and second engagement features being engageable with one another and disengageable from one another.

3. The system of claim 1, wherein the locking mechanism is on a housing of the awl and includes a pin that is biased in a first position when the locking mechanism is in the first setting and is placed under load and displaced relative to the first position when the locking mechanism is in the second setting.

4. The system of claim 3, wherein the locking mechanism includes a spring at one end of the pin to keep the locking mechanism in the first setting unless load is applied to displace the locking mechanism.

5. The system of claim 3, wherein the awl includes a shaft with a slot oriented along a length of the shaft and the pin is disposed in the slot such that when the locking mechanism is in the first setting, a ridge protruding from the pin prevents axial movement of the awl.

6. The system of claim 3, wherein the locking mechanism is a button and a shaft of the awl passes through an opening through the button.

7. The system of claim 3, further comprising a compression spring disposed in between the housing of the awl and a shaft of the awl disposed in the housing, the compression spring centered along a longitudinal axis of the shaft such that the compression spring changes in length when the shaft moves axially relative to the plate holder.

8. The system of claim 1, wherein the awl includes a shaft that extends from a first end to a second end opposite the first end, a cap being attached to the shaft at the first end, the cap sized for impaction by an impaction instrument, and the tip of the awl being at the second end of the shaft.

9. The system of claim 2, wherein the plate holder further comprises a handle with an interior surface that defines a lumen of the handle, the second engagement feature disposed on the interior surface.

10. A system comprising:
    a plate holder having a body extending from a proximal end to a distal end, two arms extending distally from the distal end and a first engagement feature; and
    an awl device including a housing having a second engagement feature engaged with the first engagement feature and a shaft including a sharp tip, the shaft partially disposed within the housing and passing through proximal and distal ends of the housing such that an entirety of the housing is in between opposite ends of an elongate dimension of the shaft,
    wherein when the second engagement feature is engaged to the first engagement feature, the awl device is partially disposed within the plate holder body, the shaft is axially translatable relative to the plate holder body to control exposure of the sharp tip while the housing and the plate holder remain immovably engaged, and the two arms of the plate holder are engageable with a bone plate, and
    wherein the awl device is disengageable from and reengagable with the plate holder.

11. The system of claim 10, wherein the first engagement feature is a protrusion on a surface of a cannulated handle surrounding the body of the plate holder and the second engagement feature is knurling on the housing of the awl.

12. The system of claim 11, wherein when the first engagement feature is engaged with the second engagement feature, at least a portion of the housing is external to the plate holder.

13. The system of claim 10, wherein the body of the plate holder includes slits that separate the body into two parts at the distal end, each part including one of the two arms, and each of the two arms including protrusions at respective free ends of the two arms, the protrusions facing each other.

14. The system of claim 13, wherein the plate holder includes a sleeve surrounding a portion of the body, the sleeve being translatable along a length of the body to control a distance between the two arms.

15. A kit comprising:
a plate holder having a first engagement feature and a second engagement feature;
an awl including a housing and a shaft disposed through the housing, the housing having a third engagement feature engageable with the first engagement feature; and
a bone plate with a fourth engagement feature engageable with the second engagement feature,
wherein the awl includes a locked setting and an unlocked setting, the locked setting fixing the shaft of the awl relative to the plate holder along a longitudinal axis of the awl and the unlocked setting allowing movement of the shaft of the awl relative to the plate holder along the longitudinal axis of the awl when the awl is subject to an impaction force, and
wherein the awl includes a first surface configured to be movable when the awl moves between the unlocked setting and the locked setting, the first surface remaining at a first distance from a proximal end of the housing in a direction parallel to the longitudinal axis while the shaft of the awl moves axially along the longitudinal axis.

16. The kit of claim 15, wherein the third engagement feature of the awl is on an outer surface of the housing of the awl, the housing being cannulated such that the shaft of the awl passes entirely therethrough and extends out of the housing from opposite sides of the housing.

17. The kit of claim 16, wherein the housing of the awl includes a button with an outer surface including the first surface, the button adjustable to toggle the awl between the locked and unlocked settings, the shaft of the awl passing through an opening in the button.

18. The kit of claim 17, wherein the shaft includes a slot having a length along a longitudinal axis of the shaft, a portion of the button passing through the slot such that the length of the slot defines a range of axial translation of the shaft of the awl relative to the housing of the awl.

19. The kit of claim 15, further comprising a screw insertion tool including a driver sized to pass through a cannulation of the plate holder.

20. The system of claim 10, wherein the shaft includes an unenclosed proximal end face actuatable to cause linear translation of the shaft relative to the housing.

* * * * *